US009731391B2

(12) United States Patent
Souza et al.

(10) Patent No.: US 9,731,391 B2
(45) Date of Patent: Aug. 15, 2017

(54) PHONE CAMERA AND SAMPLE STAND

(71) Applicant: NANO3D BIOSCIENCES INC., Houston, TX (US)

(72) Inventors: Glauco R. Souza, Houston, TX (US); Jianbo Chen, Houston, TX (US)

(73) Assignee: Nano3D Biosciences Inc., Houston, TX (US)

( * ) Notice: Subject to any disclaimer, the term of this patent is extended or adjusted under 35 U.S.C. 154(b) by 468 days.

(21) Appl. No.: 14/394,740

(22) PCT Filed: Apr. 22, 2013

(86) PCT No.: PCT/US2013/037527
§ 371 (c)(1),
(2) Date: Oct. 16, 2014

(87) PCT Pub. No.: WO2013/163059
PCT Pub. Date: Oct. 31, 2013

(65) Prior Publication Data
US 2015/0091233 A1    Apr. 2, 2015

Related U.S. Application Data

(60) Provisional application No. 61/637,108, filed on Apr. 23, 2012, provisional application No. 61/638,029, filed on Apr. 25, 2012.

(51) Int. Cl.
| | | |
|---|---|---|
| *B23Q 1/03* | (2006.01) |
| *G03B 15/00* | (2006.01) |
| *G02B 27/02* | (2006.01) |
| *G03B 17/56* | (2006.01) |
| *H04N 1/00* | (2006.01) |
| *G01N 21/25* | (2006.01) |
| *G01N 21/64* | (2006.01) |

(52) U.S. Cl.
CPC ............. *B23Q 1/03* (2013.01); *G02B 27/028* (2013.01); *G03B 15/00* (2013.01); *G03B 17/56* (2013.01); *H04N 1/00541* (2013.01); *G01N 21/253* (2013.01); *G01N 21/6452* (2013.01)

(58) Field of Classification Search
CPC ... G03B 17/561; H04N 1/00541; A47B 47/00
See application file for complete search history.

(56) References Cited

U.S. PATENT DOCUMENTS 2,634,189 A * 4/1953 Hill .................. A47L 9/009
15/246.3
3,959,803 A * 5/1976 Marvel ................ G03B 17/561
396/315

(Continued)

FOREIGN PATENT DOCUMENTS

| GB | 242196 | 11/1925 |
| JP | 2006208857 | 8/2006 |
| JP | 2008211850 | 9/2008 |

OTHER PUBLICATIONS

Search opinion of EP13781584.1.

(Continued)

*Primary Examiner* — W B Perkey
(74) *Attorney, Agent, or Firm* — Boulware & Valoir

(57) ABSTRACT

Camera phone accessories for using the camera phone to collect scientific data.

20 Claims, 13 Drawing Sheets

(56) References Cited

U.S. PATENT DOCUMENTS

| | | | | |
|---|---|---|---|---|
| 5,379,535 | A | * | 1/1995 | Bowes, Jr. ............ E02F 9/2833 37/452 |
| 5,673,983 | A | * | 10/1997 | Carlson ................. A47B 67/04 312/218 |
| 5,950,017 | A | | 9/1999 | Reff |
| 6,000,389 | A | * | 12/1999 | Alpert ................. A47J 37/0713 126/25 R |
| 6,074,027 | A | * | 6/2000 | Chang .................... A47B 47/00 312/108 |
| 7,096,936 | B1 | * | 8/2006 | Chastine ............... F25D 17/065 165/253 |
| 7,194,200 | B1 | | 3/2007 | Behlow |
| 2009/0250615 | A1 | | 10/2009 | Oldham |

OTHER PUBLICATIONS

Alter, Lloyd. Downloadable Designs: Turn Your Phone into a Scanner. Sep. 8, 2008 [online], [retrieved Jun. 13, 2013]; p. 1, image 1; p. 2, image 1 and paragraph 2. Retrieved from the Internet: <URL: http://www.treehugger.com/sustainable-product-design/downloadable-designs-turn-your-phone-into-a-scanner.html>.

* cited by examiner

Wound healing assay using HEK293 and Ibuprofen 1      2

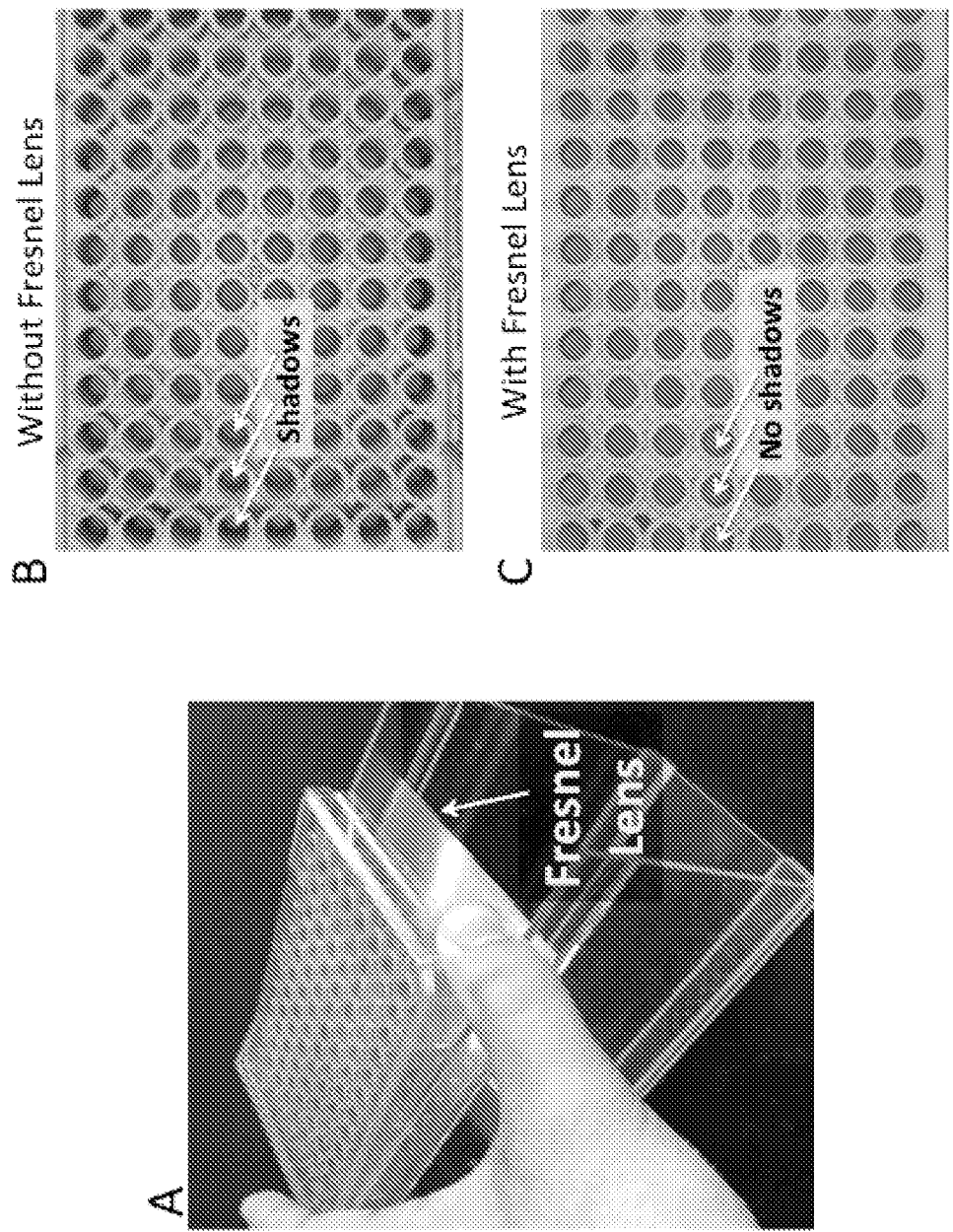
FIG. 14A-C

PHONE CAMERA AND SAMPLE STAND

PRIOR RELATED APPLICATIONS

This application claims priority to 61/638,029, filed Apr. 25, 2012, and 61/637,108, filed Apr. 23, 2012, and PCT Application No. PCT/US2013/037527, which was filed on Apr. 22, 2013, each incorporated by reference in its entirety.

FEDERALLY SPONSORED RESEARCH STATEMENT

Not applicable.

FIELD OF THE INVENTION

The invention relates to a stand that holds a laboratory or medical sample at a defined and reproducible distance from a camera phone or similar device, thus allowing a common phone to be reliably used in scientific and medical studies.

BACKGROUND OF THE INVENTION

The camera phone, like many complex systems, is the result of converging and enabling technologies. There are dozens of relevant patents dating back as far as 1956, but since the advent of the smartphone, camera phones have become both ubiquitous and highly functional. Indeed, some have estimated that there are 2.5 billion camera phones in the world, and sales are expected to top a billion per year in 2012.

For example, with the commercial success of e.g., the iPhone 4S, several features have become commonly available that make the camera phone a useful scientific tool. The iPhone 4 allows a picture to be taken from either direction (e.g., in front or behind the phone). It has a built in LED flash and can take an 8-megapixel photograph. It also has an optical zoom, and touch autofocus, and can take 1080 p video recordings. It also has face detection, video stabilization, a faster, dual core processor, support for both GSMUMTS and CDMA on one chip, GLONASS support, a natural language voice control system called Siri and is available in up to 64 GB capacity.

However, to truly realize the camera phone as a scientific tool, ancillary equipment is needed for particular scientific applications, one of which is a device to hold the phone and the lab samples at a fixed and reproducible distance from each other. The inventions described herein provide some of these accessories.

SUMMARY OF THE INVENTION

The present invention relates to a camera phone and sample stand accessory that serves to hold lab samples, such as petri plates, microtiter plates and biological specimens, in a fixed relationship to a phone camera, while still allowing access to camera controls so that a picture can be taken, and then communicated to a PC via USB port or email. We have called this device a "camstand" herein for simplicity.

Regular color photographs can be taken using the camstand, but in addition colorimetric and fluorometric assays can be performed.

Generally speaking, the camstand is a rectangular box framework with ledges sized to hold a camera and a sample at a fixed distance from each other. In preferred embodiments, the framework has ledges sized to fit common camera phones on both the top and the bottom, and one or more sample ledges at varying distances from the camera ledge(s) so that the user can select a variety of object distances from the camera.

Ledges can be omitted entirely, since the phone can sit on the bottom of the device and sample on top (or vice versa), but a plurality of ledges are preferred as they allow a variety of object distances to be selected by the user.

Further, the device can have a second set of ledges arranged at 90° to the first set. In such way the device can be turned on its side, allowing the user to select a new set of ledges, e.g., of different width, for use. In this was, the same camstand can accommodate more than one size cameraphone.

The framework can be completely open, merely having at least 10 legs needed to make a rectangular framework, together with the optional ledges, but the device can also be closed on the top and bottom for added strength. When, for example the bottom is closed, and the top open, the device is made of 4 vertical legs, 8 horizontal legs, and the base, which can also be considered a very wide leg, making a total of 9 legs. Of course, the 4 vertical legs, 8 horizontal legs can be connected with 4 perpendicular legs, thus bring the total to 12, but 9 is the minimum.

Sides can also be closed, but access is needed for the user to activate the phone and such, and thus open sides and/or ends are preferred. A completely open architecture uses the least material, provides total access and is particularly preferred.

Since the typical phone camera has a camera at one end and to one side rather than centered, and since the camera is not as wide as a microtitre plate, the ledges can be sized to reflect these parameters. Thus, a camera ledge can be much wider on one side than the other.

Optional "stops" can be added to the ledges along the length of the ledges to prevent the phone from moving past the stop, and ditto for the sample tray. Typically the phone and the sample are loaded from opposite ends of the framework, and inserted to be flush with an end or other marking or until they reach the stops.

In an alternative embodiment, every ledge is sized to fit and hold a standard microtiter plate, and a separate insert is provided that fits onto same and converts the sample ledges into the shape and size needed to hold a camera phone. This may be a preferred embodiment, since the camstand kit can thus be provided with camera ledges sized to fit the 3 or 4 major camera phones available on the market, and is also amendable to update as camera phones continue to evolve.

In preferred embodiments, there are additional ledges above the sample and phone ledges, and these serve to prevent any vertical movement of the phone or sample, but can also hold light blockers, filters, background color screens and the like.

The stand can be made of any suitable material, but plastics are preferred as lightweight, inexpensive and easily molded, but this is not essential. If the device is designed to have walls, in addition to the framework, it may be preferred to make the device of an optically clear plastic such as polycarbonate or acrylate, but where the device is just framework, the plastic can be opaque.

Suitable plastics thus include polymers, copolymers and blends of materials such as polyethylene (PE), high density PE (HDPE), polycarbonate, polyurethane, polypropylene (PP), polyvinylchloride (PVC), polymethyl methacrylate, polyvinylidene fluoride, as well as metals, alloys, ceramics and the like.

The camstand can be used with ordinary camera phones and similar devices, and when tested produce sufficiently detailed photographs to allow us to measure the size of 3D cultures grown in 96 well plates. Where additional resolution is needed, the camera can either be brought closer to the sample, or equipped with any commercially available zoom lens. Lights and filters can be used with the camstand, but we have taken scientifically usable cell culture pictures using ambient light and filters to block ambient glare or light from the screen. A Fresnel lens can also be used with the camera holder, and this has also tested well.

Additional accessories can include a cork, styrofoam (or other soft material) sample trays (shelves) that can be penetrated with pins so as to hold a biological sample, light blockers, filters, a dark background, a white background, and the like that also fit inside the frame on the appropriate ledge. Shelve with a holes therein for lens to shoot through can be provided with ridges sized to fit the major camera phones on the market. A magnifying shelf can also be provided, where the hole is replaced with a 2×, 4×, etc. magnifying lens, allowing magnification of the picture, although some cameras already offer a zoom feature.

In further detail, the invention is a phone camera and sample stand kit, said kit comprising a first two vertical legs connected to a first two horizontal legs so as to form a first rectangle, a second two vertical legs connected to a second two horizontal legs so as to form a second rectangle, said first rectangle and said second rectangle connected at a base so as to form a rectangular box with an open top and a plurality of pairs of matched ledges on said vertical legs and parallel to said horizontal legs and forming shelf ledges inside of said rectangular box frame, said ledges being wide enough to hold, for example, a 3⅜ inch plate or other common scientific apparatus.

In addition to a rectangular framework, the frame could be any parallelepiped, including cube (six square faces), and the rhombohedron (six rhombus faces), or rhomboid (six parallelograms), but most often will have 4 rectangular faces, and two cube faces.

The various components or accessories sold with the camstand can vary, but might include one or more of a first solid shelf that removably fits on said pairs of ledges, said first solid shelf having a lens hole therein at a position appropriate for a camera phone; a second solid shelf that removably fits on said pairs of ledges, at least one third solid shelf that removably fits on said pairs of ledges and is at least 2 mm thick and soft enough to penetrate with a pin; at least one fourth solid transparent shelf that is a light filter; and at least one fifth solid shelf having a hole therein fitted with a magnifying lens, and at least one fifth solid shelf being a Fresnel lens or having a Fresnel lens covering a hole therein.

In another embodiment, the invention is a phone camera and sample stand comprising: a first two vertical legs connected to a first two horizontal legs so as to form a first rectangle, a second two vertical legs connected to a second two horizontal legs so as to form a second rectangle, said first rectangle and said second rectangle connected by at least one perpendicular leg so as to form a rectangular box frame, pairs of matched ledges on said vertical legs and parallel to said horizontal legs and forming shelf ledges inside of said rectangular box frame. As above, the camstand includes one or more accessories, including a first solid shelf that removably fits on said pairs of ledges, said first solid shelf having a lens hole therein. A second solid shelf that removably fits on said pairs of ledges. A third solid shelf that removably fits on said pairs of ledges, wherein said removable solid shelf is at least 2 mm thick and is soft enough to be penetrated with a pin. A fourth solid shelf that removably fits on said pairs of ledges, wherein said removable solid shelf has a drop down leaf removably attached at one end, and affixed at an another end to the solid shelf.

One or more removable transparent filters sized to fit on one of said pair of ledges can also be provided. Alternatively, removable transparent filters that removably fit on said lens hole of said removable solid shelf can be provided. Black or white opaque shelves removably fitting on said matched ledges can be included. Another solid shelf that removably fits on said pairs of ledges can be provided, wherein said solid shelf has a hole fitted with a magnifying lens of conventional or Fresnel type. The lens can be permanently or removably affixed, and if removably fitted, e.g., via snap fit, a number of lens strengths can be included in the kit, such as 1.5×, 2×, 4×, etc.

One or more shelves can have ridges on a surface thereof sized to hold a camera phone so that the lens of said camera phone sits over said lens hole. There can also be ridges thereon sized to hold a standard microtiter plate adjacent to at least one perpendicular leg. The ridges for the different uses can be on opposite faces of said shelves. The ridges can also vary in placement so as to fit a variety of standard scientific apparatus and phone sizes. The components can also be sold via menu, the buyer selecting which items to include with his or her camstand, thus building a custom camstand kit for a particular purpose.

In another embodiment, the invention is a camstand kit, comprising a rectangular box frame having pairs of matched ledges for holding removable shelves thereon, and at least one solid removable shelf, and at least one solid removable shelf having a lens hole therein. A variety of accessories can be included, as described above.

Although we have described the holder as sized to fit a camera phone, we do not mean to limit the size of the device, except as expressly stated herein, as the same principles can be used together with any tablet also containing camera features. Thus, an I-pad® sized holder can be made and function in the same way.

BRIEF DESCRIPTION OF THE DRAWINGS

FIG. 3A-B. Perspective view of the camstand, wherein FIG. 3A shows a single phone ledge and a single camera ledge, each with stops at the appropriate location, and FIG. 3B shows a series of ledges, all sized to fit a standard microtitre plate and separate camera adaptor ledges (rectangular with large opening for lens) that can be placed on any sample ledge and hold the camera, allowing the lens an unobstructed view through the large lens opening.

FIG. 10 shows another embodiment of a sample tray with a drop down leaf that functions to block light from the camera screen impinging on the wells, and interfering with the photo.

FIG. 14. A camera holder with Fresnel lens positioned just below the 96 well plate. During the process of taking pictures, the 96 well sits directly on top of the lens sheet. B. Image taken with the holder without the Fresnel lens, clearly showing the shadow at the outside wells. C. Image taken with the holder and with the Fresnel lens in place showing a much clear image than in B, without shadows.

DESCRIPTION OF EMBODIMENTS OF THE INVENTION

Generally speaking the invention relates to a cell phone camera and sample stand and related accessories, wherein the "camstand" has a rectangular box or parallelepiped framework and ledges sized to hold phone and/or samples steadily and at a reproducible distance from the sample.

Figure 1:
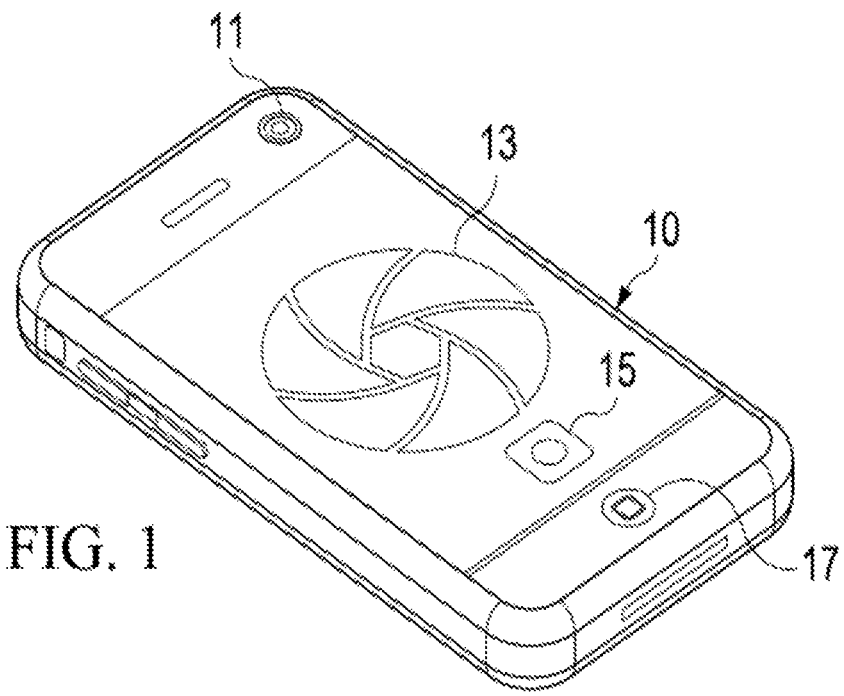
FIG. 1. Perspective view of a typical touch screen camera phone.

FIG. 1 shows a typical touch screen cell phone 10 showing camera 11, shutter image 13, camera activation image 15, and cell phone control or menu button 17.

Figure 2:
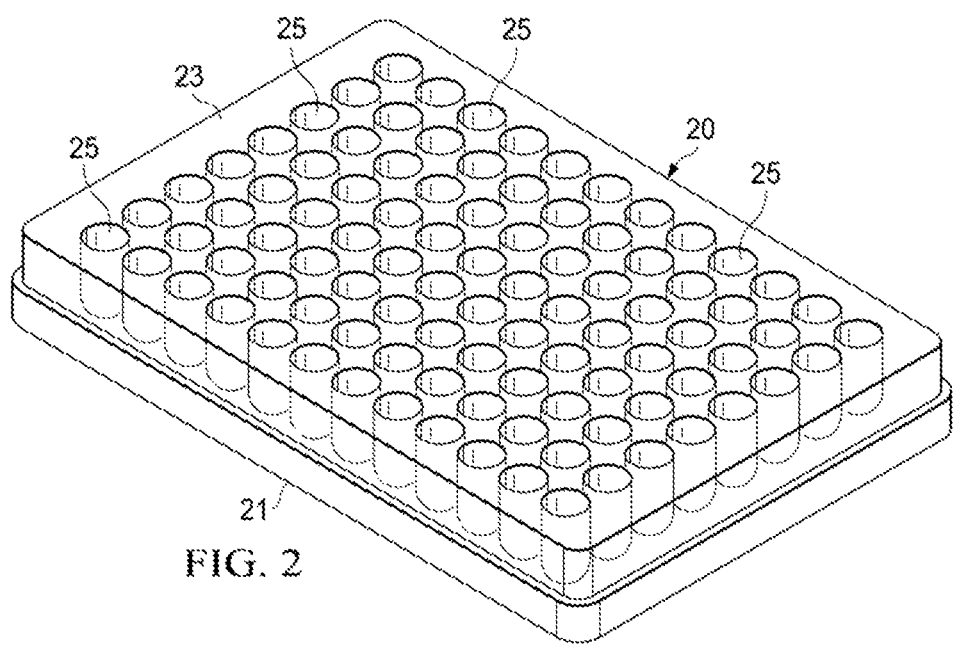
FIG. 2 Perspective view of a typical microtiter plate.

FIG. 2 shows the typical microtitre plate 20 with base 21, top 23 and multiple wells 25. These are of standard size (about 5 inch×3/14 inch), and a preferred camstand is sized to hold same.

Figure 3A:
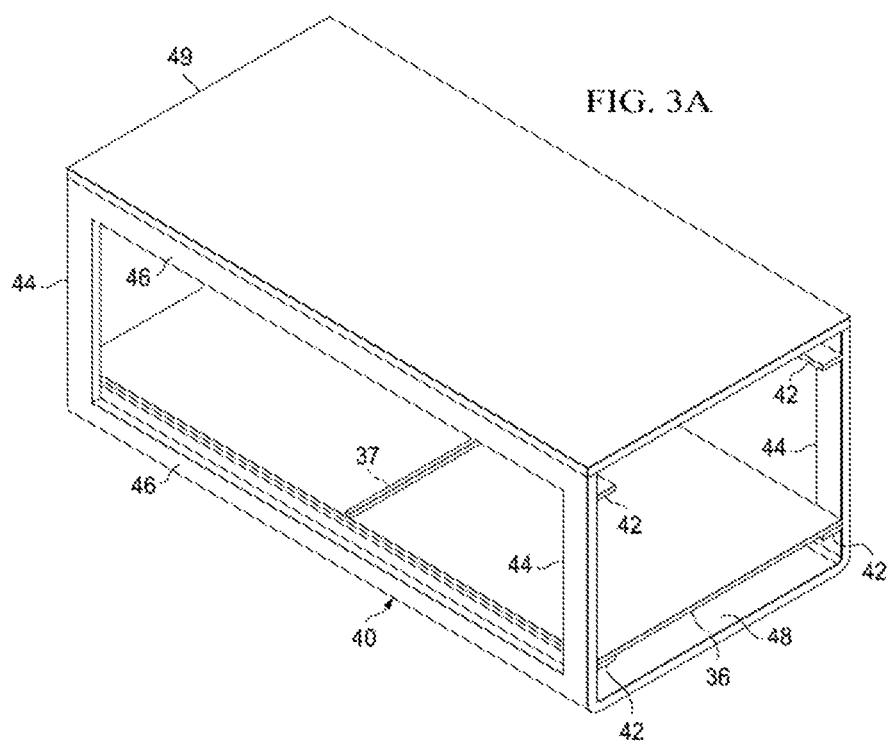

FIG. 3A shows one embodiment of camstand 40 having 4 vertical legs 44 connected to 4 horizontal legs 46 and 2-4 (2 shown here) perpendicular legs 48 and 49 connecting the frame into a rectangular shaped box frame. In this instance, legs 49 and 48 cover the entire top and bottom surfaces, rather than being merely end legs, but as noted herein, this is optional. Upper ledges 42 are specially sized to hold a standard microtitre plate a particular distance from the camera, which can sit on the bottom of the camstand or on a ledge or on a removable shelf fitted onto a ledge. In the embodiment shown, shelf 36 fits on lower ledge 42, provides a surface for the camera to sit on, and positions the camera closer to the sample than would be achieved if the camera were placed on the bottom of the camstand. A stop or ridge 37 is placed on the shelf 36 to indicate where the camera should stop so as to place the lens about midway. An additional ridge (perpendicular to ridge 37) can be placed on the shelf to stop lateral movement of the camera as well.

Figure 3B:
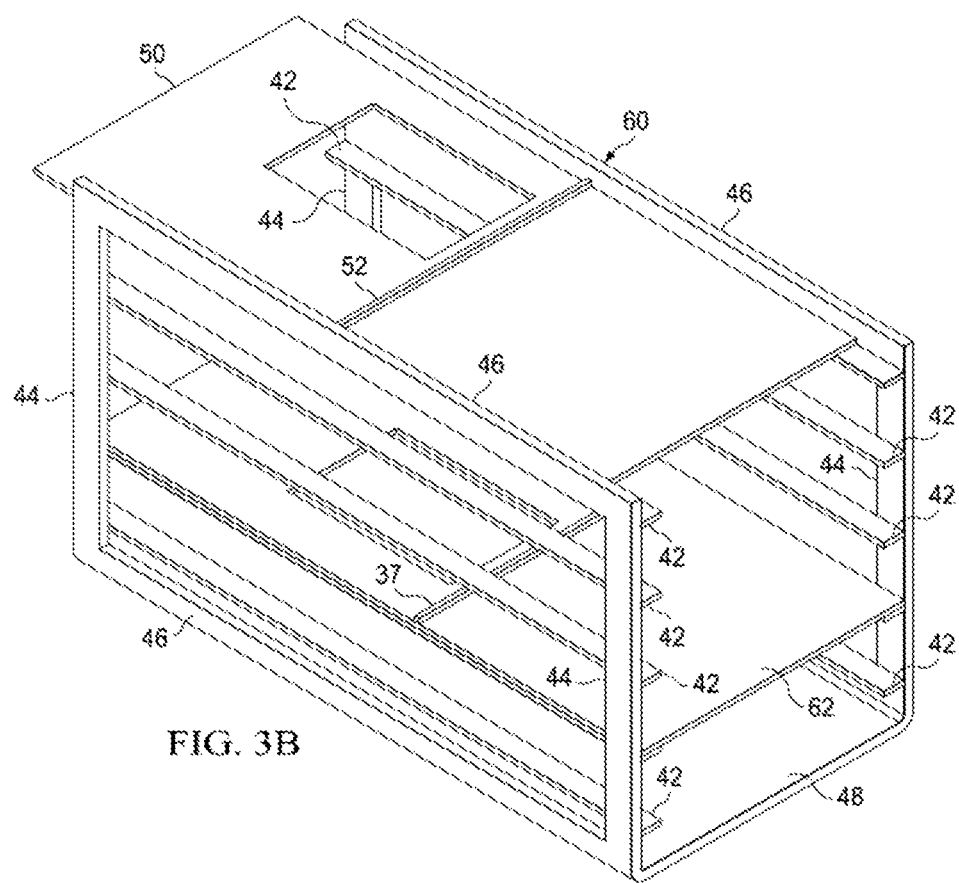

FIG. 3B shows another embodiment where there are 4 vertical legs 44 connected to 4 horizontal legs 46 and 1-4 (1 shown here) perpendicular legs a.k.a. base 48 connecting the frame into a rectangular shaped box frame. In this variation, there are several ledges 42 positioned along vertical legs and the camera shelf 62 can be placed at any of these positions, thus controlling the distance to the sample. In this example, shelf 50 has a hole through which photos can be taken in a downward direction, as well as a ridge or stop 52 to position the camera. Using shelf 50 in an upper position as shown, the sample can be below the camera on any of the remaining ledges 42. Alternatively, the camera can be placed on shelf 62, the upper shelf 50 removed and replaced with sample and the photo taken upwards.

Figure 4:
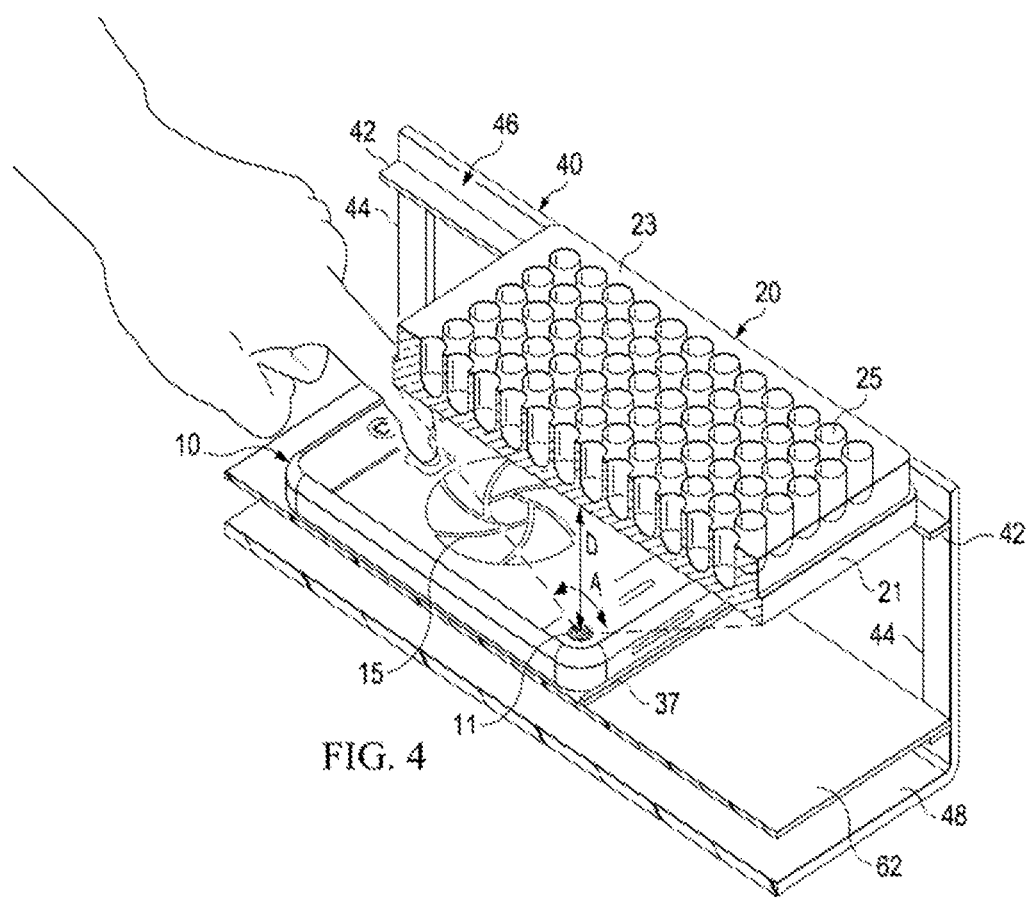
FIG. 4. Cross section of camstand along long axis, showing relationship of phone to sample, as well as object distance D and viewing angle A.

FIG. 4 shows one example of this wherein only half the device is shown for clarity. The camera sits on shelf 62, pushed into the box to rest against stop 37. A plate 20 is placed on an upper ledge 42 at a distance D from the camera. The larger the distance D, the greater the angle of view A that can be photographed. A user can put his or her finger inside the camstand to activate the camera, thus taking a picture of the bottom of the plate.

Improved image resolution can be achieved by moving the camera closer to the object, but this comes at the loss of capturing the entire object in a single shot. If improved resolution is needed, one can still capture the image of the entire object by using two cameras at the bottom to capture the images. The two cameras could be positioned opposite of each other on the same plane/height with field of view that captures halves of the object. Alternately, automation can be incorporated to this system by having a mechanical and/or electrical actuator that steps or translates the camera from one side to the other to capture parts of the object.

Figure 5A:
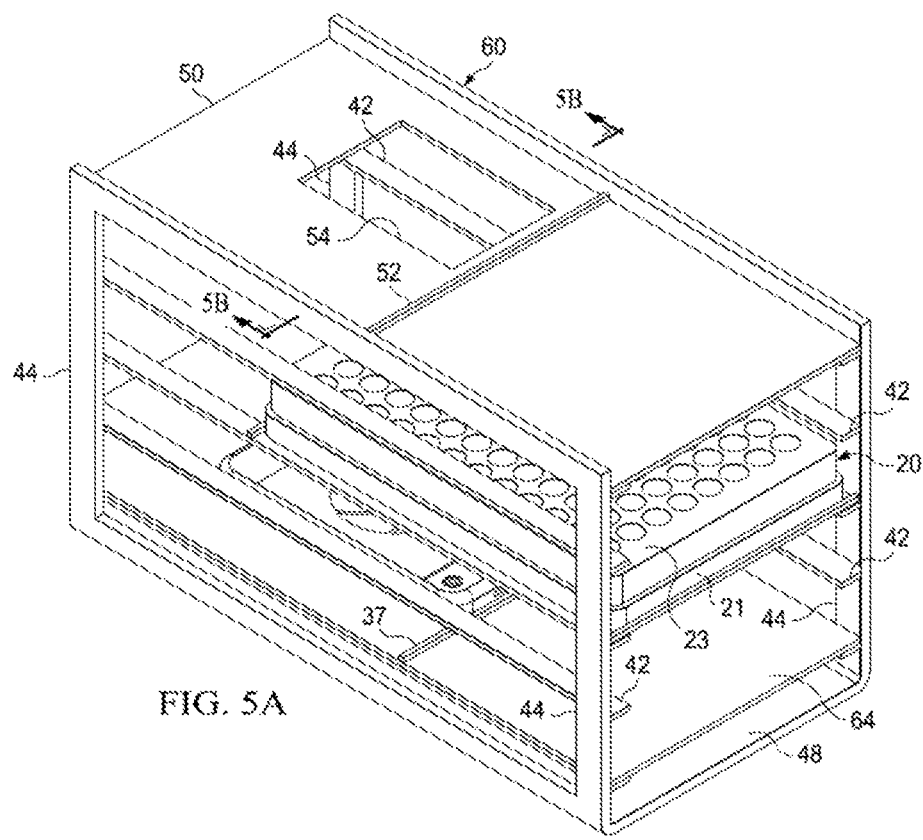
FIG. 5A-B. Perspective view 5A and end view 5B of camstand showing phone on the bottom shooting a petri plate above.

FIG. 5A shows another embodiment, wherein the device has an open end and a closed end 48, and the device can be used either side up. Here shown, the closed end 48 is on the bottom, and the plate 20 is positioned in the middle, and the camera can be placed above the plate 20 on shelf 50 with lens hole 54, or below the plate 20 on shelf 64. In this case, the camera has been placed on lower shelf 64 and pushed in until meeting stop 37, thus allowing the camera to shoot upwardly. Shelf 64 position can be varied, as can plate 20 position, by selecting different ledges 42 for use. Thus, the camera object distance can be controlled.

Figure 5B:
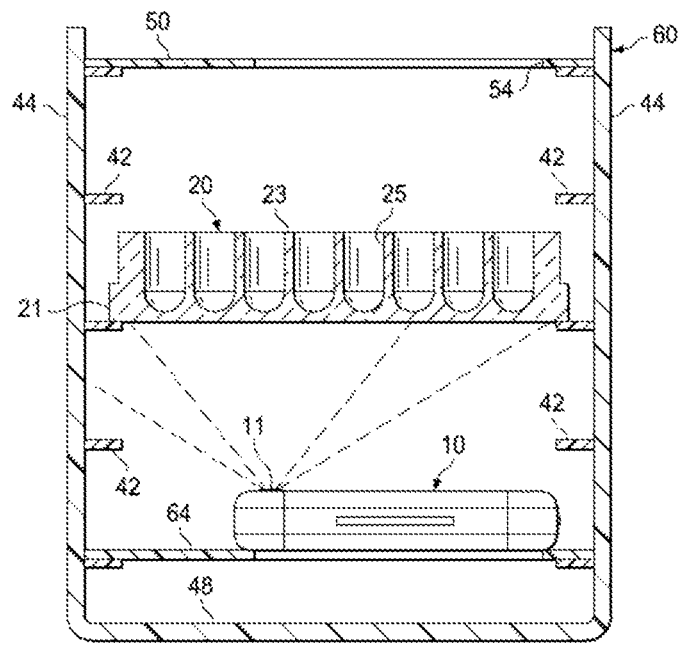

FIG. 5B shows a cross sectional end view through the device of FIG. 5A, wherein vertical legs 44 have ledges 42 thereon and are sized to hold sample trays or plates, such as microtitre plate 20 having walls 23 and base 21 forming a plurality of wells 25. Camera cell phone 10 is positioned below the plate 20 on movable shelf 64 which can have edges or ridges on it to hold the camera in the correct position (ridges not seen). If the sample was even larger than a microtitre plate, it could be placed on the top of the unit, which in this version has an open top, and the camera moved closer as needed. If desired to shoot from above, the camera would be placed on movable shelf 50 having hole 54, and the lens 11 positioned so as to shoot down through hole 54.

Figure 6A:
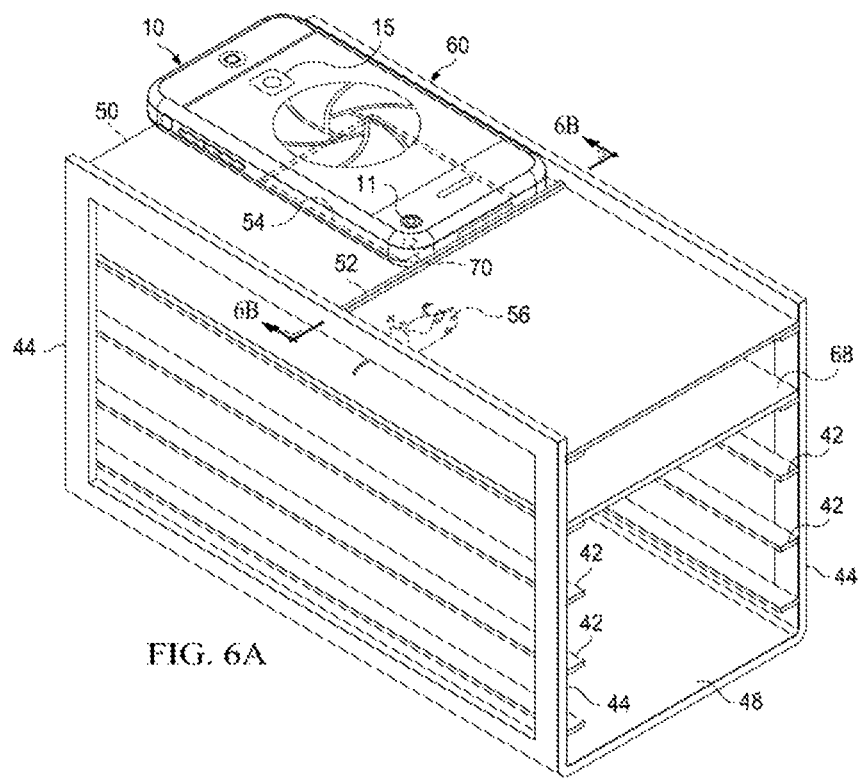
FIG. 6A-B. Perspective view 6A and end view 6B of camstand showing phone on the top shooting a surgically opened mouse on middle sample ledge. When the mouse is closer to the camera, higher resolution will be available, and for larger samples the sample can be moved to a ledge at greater distance.

A top down embodiment is shown in FIG. 6A, which shows the camera on upper shelf 50, and sample (in this case a mouse 56) on a lower shelf 68, with lens 70 position over hole 54. For a larger view, the mouse shelf can of course be lowered to a lower set of ledges 42. If needed, a macro lens can be added to the camera, and inexpensive lens adaptors are available for cell phones. Alternatively, one can be provided as a component of a removable shelf, e.g., a magnifying lens can be incorporated into shelf 50, over hole 54.

In another embodiment, a filter can be provided at the hole 54 such that the images taken by the phone have been filtered. The filter can be a transparent colored filter, depending on the effect to be achieved. A black or white or colored filter helps to filter the ambient light shedding to the sample.

The filter can be integrated to the shelf 50, or alternatively it can be another removable element specifically fit to the hole 54 by means of, for example, rails for sliding in the filter or snap fit mechanisms. Other filters for different purposes can also be provided. The filters can also be shelf sized, rather than fitted to the hole.

Figure 6B:
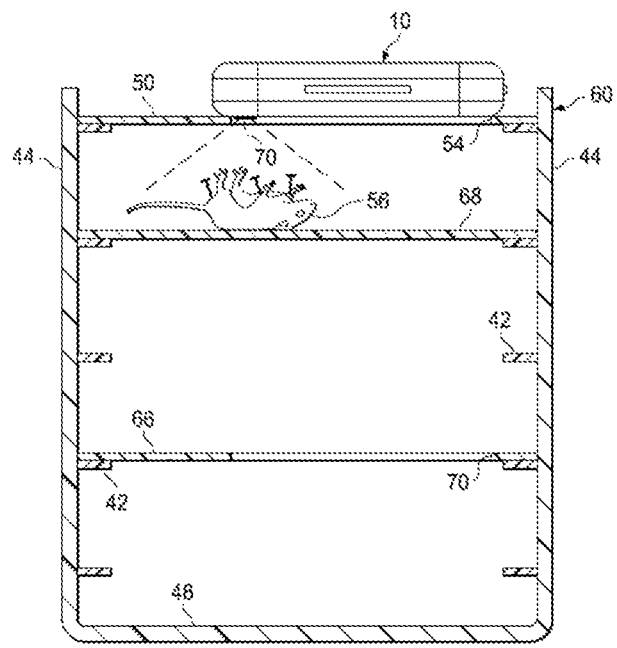

FIG. 6B shows the embodiment of FIG. 6A in cross section, allowing a close up photograph of mouse 56. While we prefer a shelf 50 with hole 54, it is also possible to size at least the bottom set of ledges so that a shelf is not needed. Thus, the ledges can be big enough on one side so as to hold the camera at a central location. Alternatively, and as already discussed, the camera can sit on closed base 48.

Figure 7:
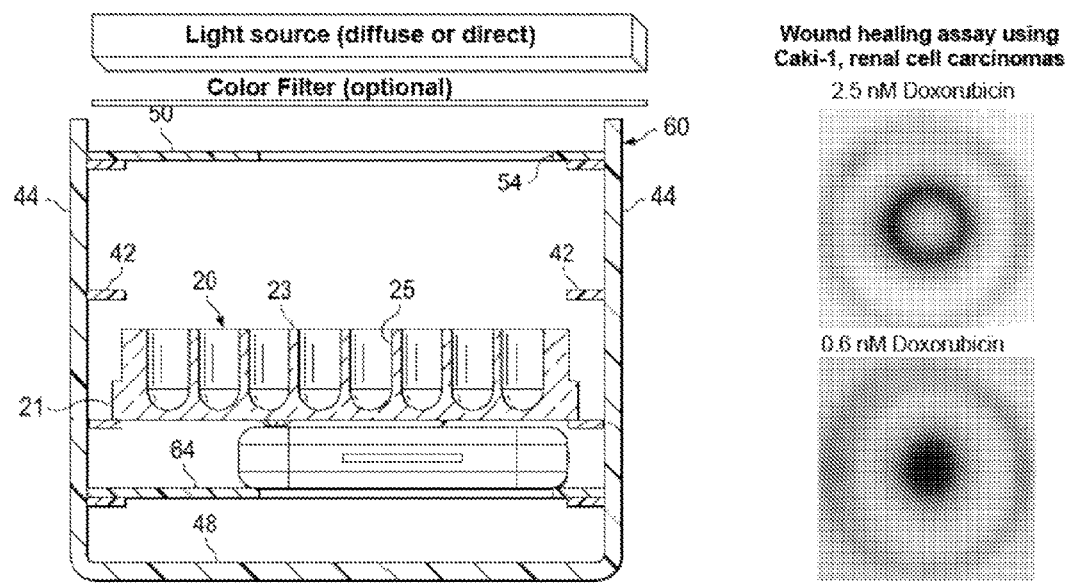
FIG. 7 shows the camstand in use, wherein the left hand panel shows the set up for taking close photographs of a single microwell. Actual data is shown on the right.
Figure 8:
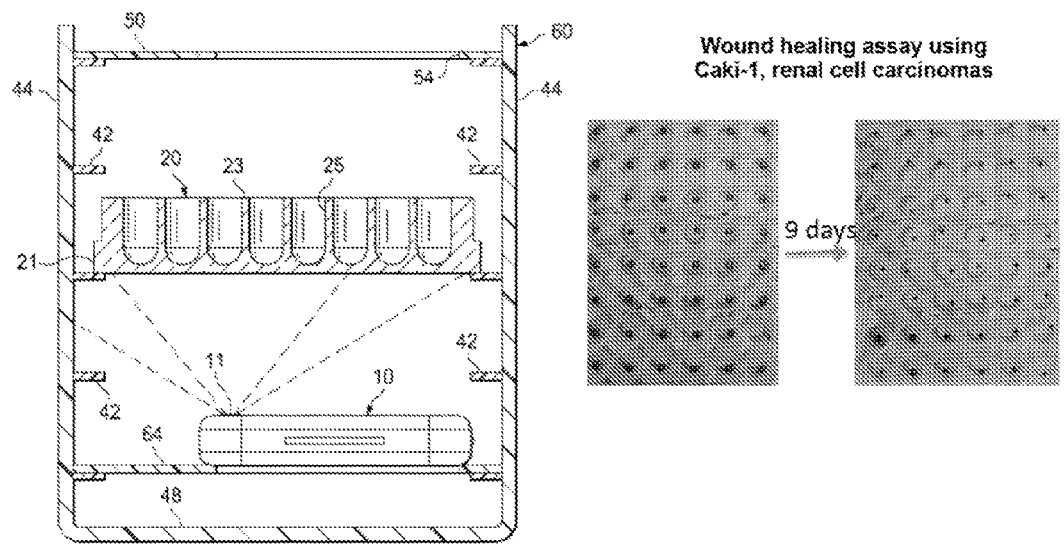
FIG. 8 shows another example of the camstand in use, wherein the left hand panel shows the set up for taking a wider photograph of an entire microwell plate. Actual data is shown on the right.
Figure 9:
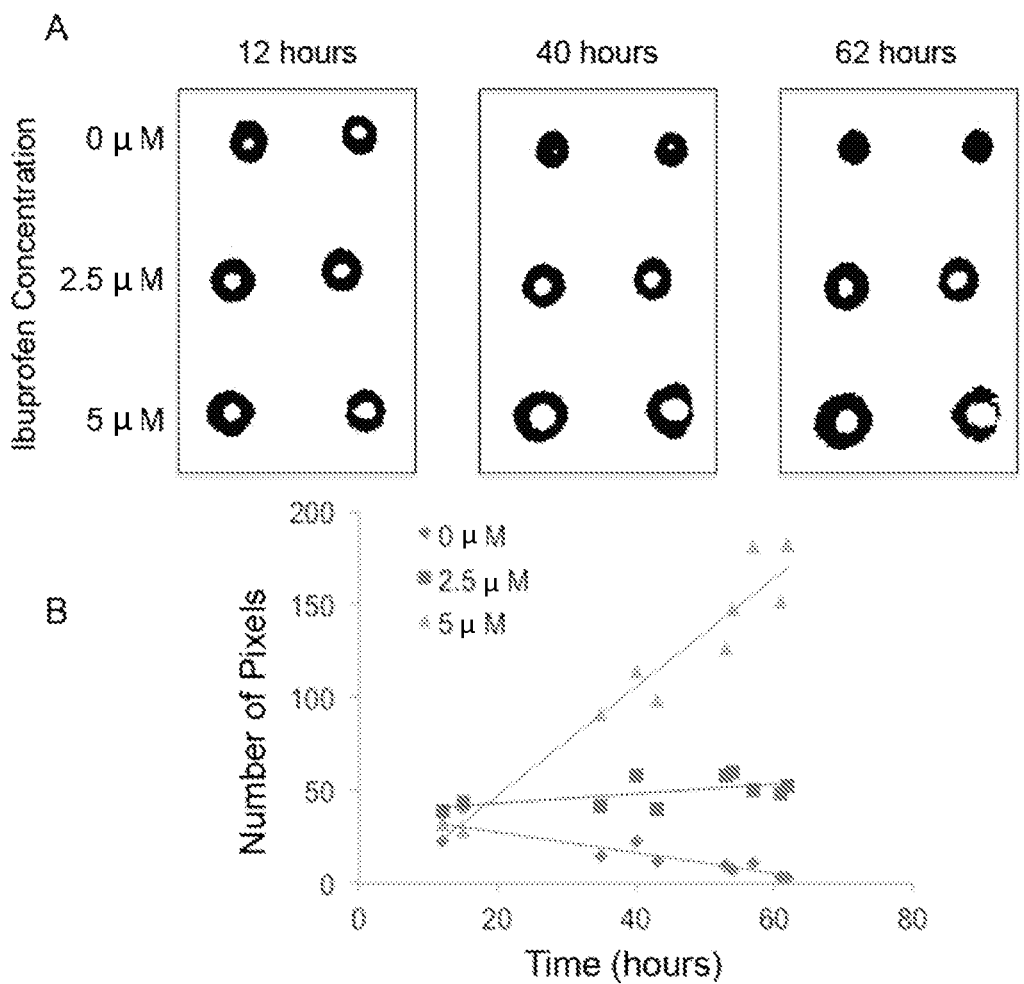
FIG. 9 shows exemplary data analysis using the camstand, wherein a schematic of a wound closing assay is shown in FIG. 9A and the data is graphed in FIG. 9B.
Figure 1O:
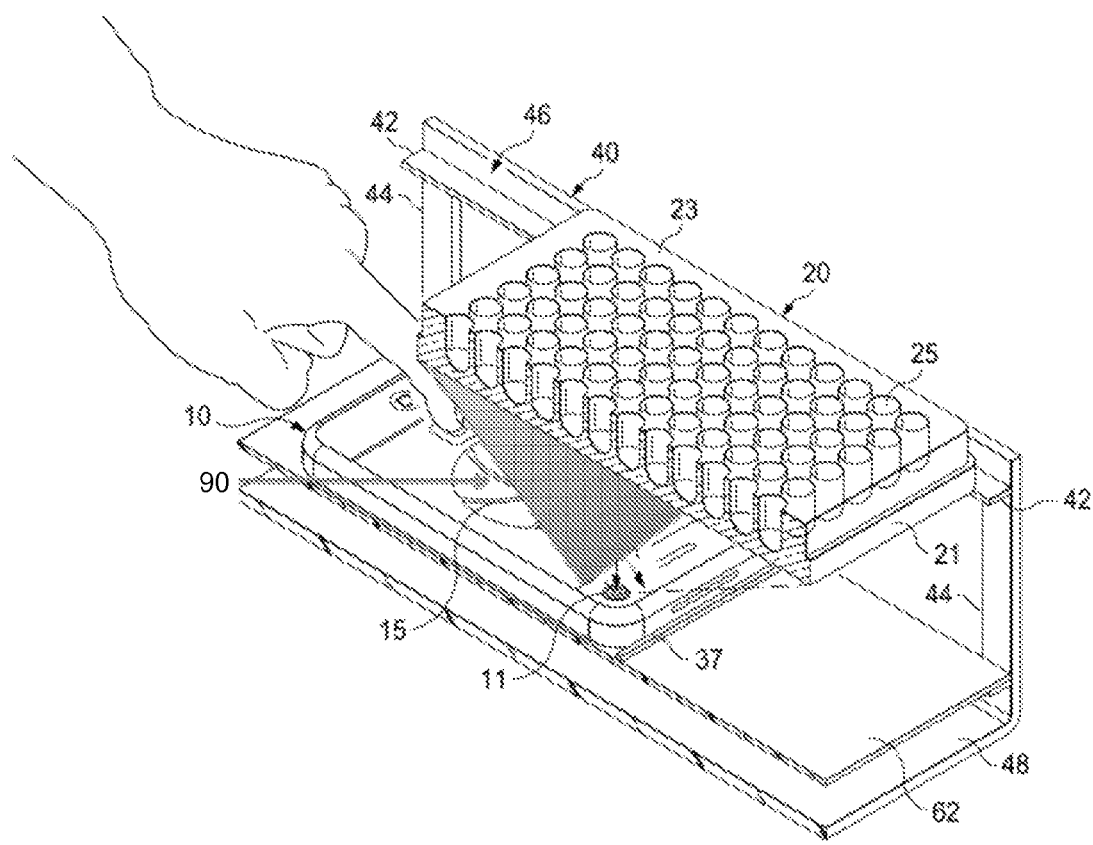

FIGS. 7-9 show examples of the camstand in actual use, proving that the system is accurate enough for scientific studies. In FIG. 7, images on the right were collected with iPhone directly below microwell of a 96-well plate, This general approach could be modified for having an array of detectors, where each detector is dedicated to and/or direct under each well. Alternatively, the detector (iPhone) could also be placed on a translation stage which could be translated (x,y) from well-to-well for capturing images. The same can be true for light sources, each well could have a diode (or laser light, and/or fiber guided light). If needed, automation can be incorporated to this system by having a mechanical and/or electrical actuator that translates the camera to take pictures of each well. Alternatively, this concept of placing the camera directly below the probed microwell can be further implemented as an array of optical detectors placed directly below each or a combination of adjacent microwells.

FIG. 10 shows another example of a shelf with a drop down leaf 90 that functions as a light barrier, blocking camera screen light, while still allowing touch access to the camera screen. The barrier 90 could be directly above the screen, but it would be ideal to have access to the screen for touch-screen focus selection if needed. A simple catch (not shown), can hold the leaf in the up position (against the shelf) when not in use.

Figure 11:
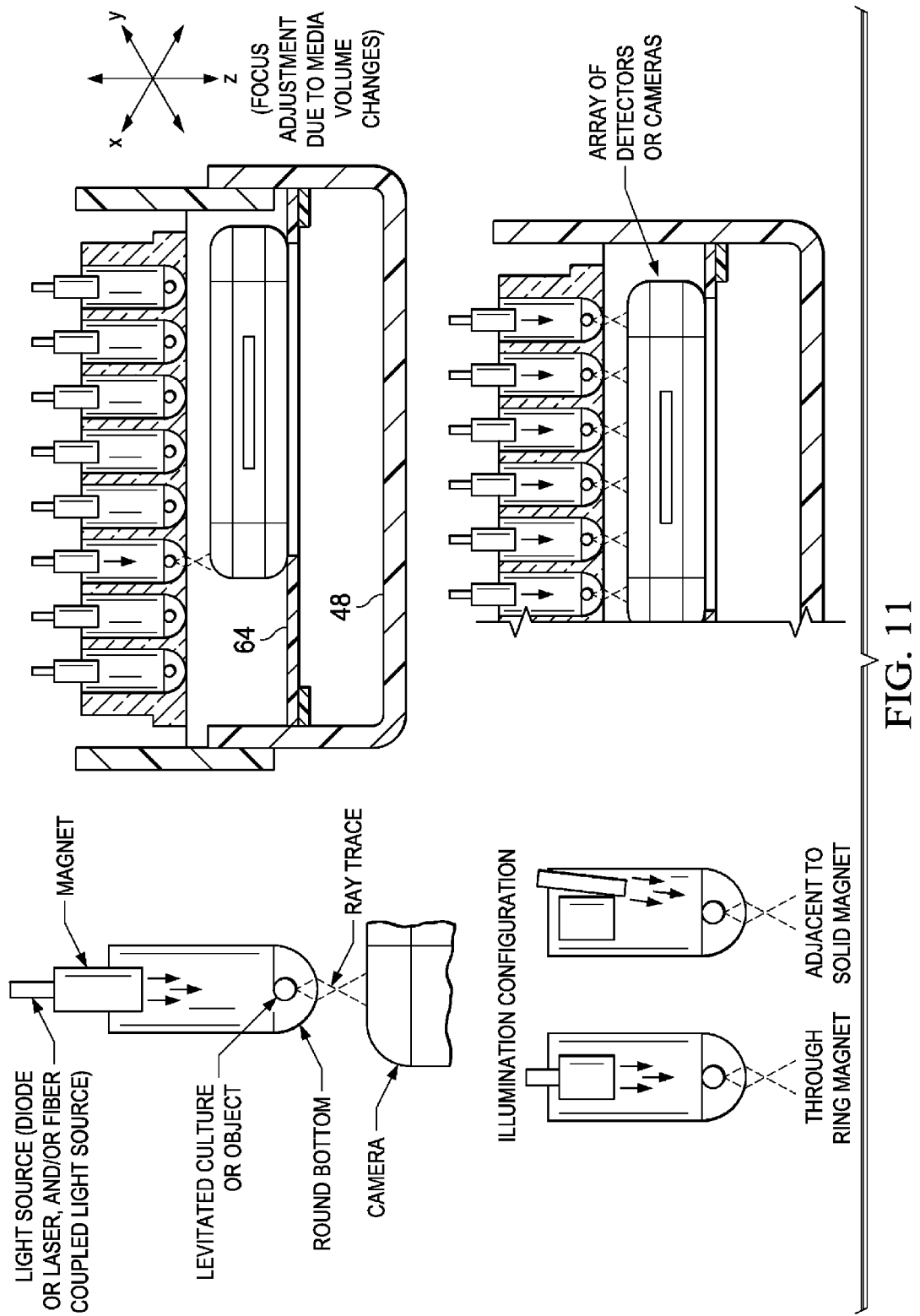
FIG. 11. Shows magnetically levitated cells, moving cells off the bottom of the round well bottom, for better focus.

FIG. 11 shows examples of using round bottom 96 well plates to levitate images on a camera or optical detector. Levitation of cells off the bottom of a curved surface allows image distortion due to the curvature of the bottom of round bottom microwell plates and changes in refractive index between media, plastic, and air to be refocused and magnified. Levitated or floating objects can be refocused and magnified away from the surface andor away from the focal point of the round bottom or lens. The curvature and the material of the bottom of the curved surface can be modified to match optical quality and focusing requirements of phone camera or detector array.

One preferred lens is a Fresnel lens, which is a type of compact lens that provides the same function as a conventional lens. However, the serrated surface design allows the construction of lenses of large aperture and short focal length without the mass and volume of material that would be required by a lens of conventional design. A Fresnel lens can be made much thinner than a comparable conventional lens, in some cases taking the form of a flat sheet. A Fresnel lens can capture more oblique light from a light source.

Figure 12:
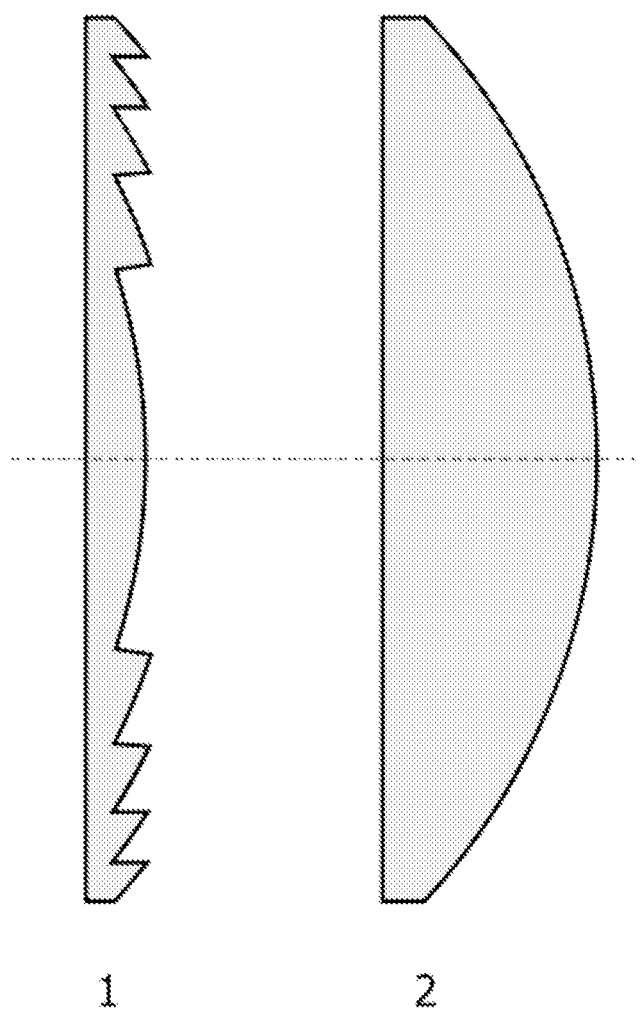
FIG. 12. Cross section of a spherical Fresnel lens (1) which has light bending properties comparable to the conventional lens (2) on the right.

The Fresnel lens reduces the amount of material required compared to a conventional lens by dividing the lens into a set of concentric annular sections. In each section, the overall thickness is decreased compared to an equivalent simple lens. This effectively divides the continuous surface of a standard lens into a set of surfaces of the same curvature, with stepwise discontinuities between them (FIG. 12).

Figure 13B:
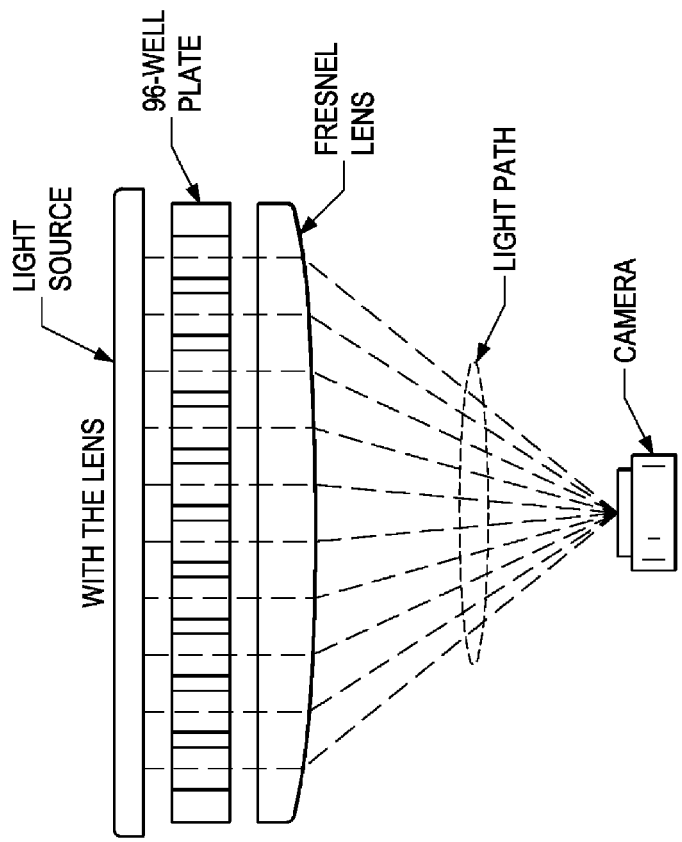
FIG. 13B. Same side view of illumination of the plate used with a Fresnel lens. The light bending pattern illustrated eliminates shadows in the plate.
Figure 13A:
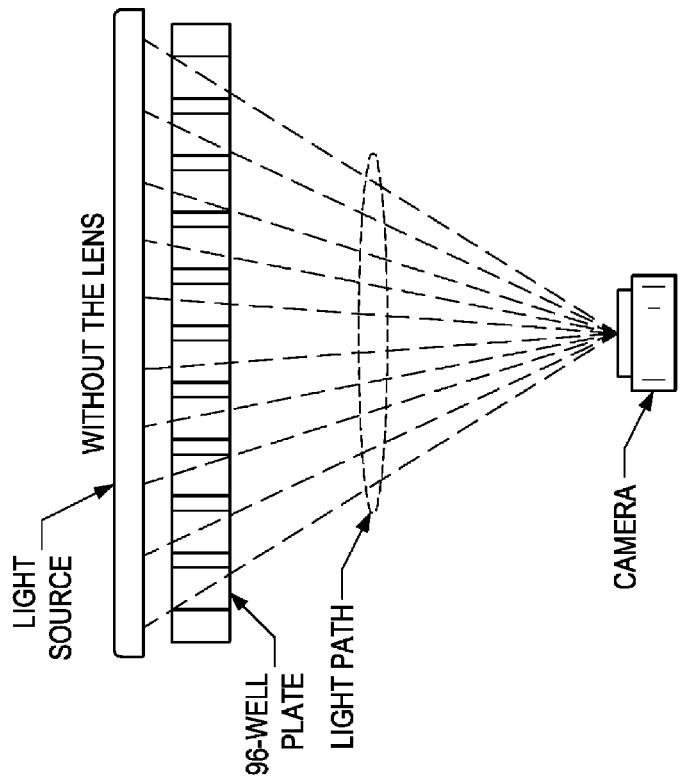
FIG. 13A. Side view of illumination of a plate when there is no lens used. Camstand omitted for simplicity.

The reason for using a Fresnel lens for the image system is that there is a need to bend the light in order to reduce shadow. The lens will help collecting the light pass straight through the wells so it will not be blocked by the edge of the well, thus we are able to decrease the shadow area of the image that taken by various camera devices. The details of the mechanism are illustrated in the FIG. 13.

Each lens has a focus length. One preferred lens has 3× magnification, which equals to a focus length of 300 mm, but lens of 2×, 5× to 10× or more could be used. The lens is placed right beneath the culture plate.

Ideally a perfect image that captures nothing but the cell structure of each well would be obtained if the distance between the lens and the camera is 300 mm. However, the distance may be limited by the dimensions of the box or holder. In such case, another lens can be used to further shorten the focus distance to a range comparable to the existing dimensions of the holder. The new focus length is calculated using the following equation.

$$1/f = 1/f_1 + 1/f_2$$

Thus, the new focal length is 150 mm, which is close to the distance between the lens and the camera (105 mm). To further optimize the image quality, we could customize the Fresnel lens with 105-110 mm focal length; by doing that we can obtain minimum shadow and the best images.

FIG. 14 shows an camera holder with a Fresnel lens positioned just below the 96 well plate. During the process of taking pictures, the 96 well sits directly on top of the lens sheet. B. Image taken with the holder without the Fresnel lens, clearly showing the shadow at the outside wells. C. Image taken with the camstand and with the Fresnel lens in place showing a much clear image than in B and without shadows.

What is claimed is:

1. A phone camera and sample stand kit, said kit comprising
   a) a first two vertical legs connected to a first two horizontal legs so as to form a first rectangle, a second two vertical legs connected to a second two horizontal legs so as to form a second rectangle, said first rectangle and said second rectangle connected at a base so as to form a rectangular box frame with an open top and a plurality of pairs of matched ledges on said vertical legs and parallel to said horizontal legs and forming shelf ledges inside of said rectangular box frame, said ledges being wide enough to hold a 3⅜ inch plate;
   b) a first solid shelf that removably fits on said pairs of ledges, said first solid shelf having a lens hole therein at a position appropriate for a camera phone;
   c) a second solid shelf that removably fits on said pairs of ledges,
   d) at least one third solid shelf that removably fits on said pairs of ledges and is at least 2 mm thick and soft enough to penetrate with a pin;
   e) at least one fourth solid transparent shelf that removably fits on said pairs of ledges that is a light filter; and
   f) at least one fifth solid shelf that removably fits on said pairs of ledges having a hole therein fitted with a magnifying lens.

2. A phone camera and sample stand comprising:
   a) a first two vertical legs connected to a first two horizontal legs so as to form a first rectangle, a second two vertical legs connected to a second two horizontal legs so as to form a second rectangle, said first rectangle and said second rectangle connected by at least one perpendicular leg so as to form a rectangular box frame,
b) pairs of matched ledges on said vertical legs and parallel to said horizontal legs and forming shelf ledges inside of said rectangular box frame,
c) further comprising a first solid shelf that removably fits on said pairs of ledges, said first solid shelf having a lens hole therein.

3. The phone camera and sample stand of claim 2, further comprising a second solid shelf that removably fits on said pairs of ledges.

4. The phone camera and sample stand of claim 2, said first solid shelf having ridges on a surface thereof sized to hold a camera phone so that the lens of said camera phone sits over said lens hole.

5. The phone camera and sample stand of claim 2, further comprising a third solid shelf that removably fits on said pairs of ledges, wherein said removable solid shelf is at least 2 mm thick and is soft enough to be penetrated with a pin.

6. The phone camera and sample stand of claim 2, further comprising a fourth solid shelf that removably fits on said pairs of ledges, wherein said removable solid shelf has a drop down leaf removably attached at one end, and affixed at an another end to the solid shelf.

7. The phone camera and sample stand of claim 3, wherein said second removable solid shelf has a ridge thereon sized to hold a standard microtiter plate adjacent to at least one perpendicular leg.

8. The phone camera and sample stand of claim 2, said rectangular box frame being of width to hold a standard microtitre plate.

9. The phone camera and sample stand of claim 2, wherein a camera lens can shoot through said lens hole of said first solid shelf, and said first solid shelf further comprises ridges on one surface thereof sized to hold a standard microtiter plate adjacent to one of said perpendicular leg and ridges on an opposite surface thereof to hold a camera such that said lens fits over or under said hole and adjacent to an opposite perpendicular leg.

10. The phone camera and sample stand of claim 2, further comprising one or more removable transparent filters sized to fit on one of said pair of ledges.

11. The phone camera and sample stand of claim 2, further comprising a separate Fresnel lens sized to fit on one of said pair of ledges.

12. The phone camera and sample stand of claim 2, further comprising one or more removable transparent filters removably fit on said lens hole of said removable solid shelf.

13. The phone camera and sample stand of claim 2, further comprising a third solid shelf that removably fits on said pairs of ledges, wherein said solid shelf has a hole fitted with a magnifying lens.

14. A camera and sample stand kit, said kit comprising
a) an open parallelepiped framework having a plurality of pairs of shelf ledges inside of said parallelepiped framework;
b) a first solid shelf that removably fits on said pairs of shelf ledges, said first solid shelf having a lens hole therein at a position appropriate for a phone;
c) a second solid shelf that removably fits on said pairs of shelf ledges,
d) at least one third solid shelf that removably fits on said pairs of shelf ledges and is at least 2 mm thick and soft enough to penetrate with a pin;
e) at least one fourth solid transparent shelf that removably fits on said pairs of shelf ledges that is a light filter; and
f) at least one fifth solid that removably fits on said pairs of shelf ledges and being fitted with a magnifying lens.

15. A camstand kit, comprising a rectangular box frame having pairs of matched ledges for holding removable shelves thereon, and at least one solid removable shelf, and at least one solid removable shelf having a lens hole therein, further comprising a transparent colored filter fitting on said matched ledges.

16. The camstand kit of claim 15, further comprising a solid removable shelf of at least 2 mm thickness, and comprising a material soft enough to be penetrated with a pin.

17. The camstand kit of claim 15, further comprising a removable filter that fits on said lens hole of said solid removable shelf.

18. The camstand kit of claim 15, further comprising a solid removable shelf having a hole therein, wherein said hole is fitted with a magnifying lens.

19. The camstand kit of claim 15, further comprising a Fresnel lens fitting on said matched ledges.

20. The camstand kit of claim 15, further comprising a solid shelf that removably fits on said pairs of ledges, wherein said removable solid shelf has a drop down leaf removably attached at one end, and affixed at an another end, to said solid shelf.

* * * * *